United States Patent [19]
Murphy et al.

[11] Patent Number: 5,958,751
[45] Date of Patent: Sep. 28, 1999

[54] α-GALACTOSIDASE

[75] Inventors: Dennis Murphy, Paoli; John Reid, Bryn Mawr, both of Pa.

[73] Assignee: Diversa Corporation, San Diego, Calif.

[21] Appl. No.: 08/613,220

[22] Filed: Mar. 8, 1996

[51] Int. Cl.⁶ .......................... C12N 15/09; C12N 15/56; C12N 9/40
[52] U.S. Cl. .................. 435/208; 435/320.1; 435/252.3; 435/325; 435/419; 536/23.2; 536/24.32
[58] Field of Search .................................. 435/208, 320.1, 435/252.3, 325, 419; 536/23.2, 24.32

[56] References Cited

PUBLICATIONS

Keller, et al., "Thermococcus alcaliphilus sp. nov., a new hyperthermophilic archaeum growing on polysulphide at alkaline pH.," *Archives of Microbiology*, 1995, vol. 164, pp. 390–395.

Sakka et al. Biosci. Biotech. Biochem. 57(2):273–277, 1993.

Genbank Database Record NID g3236129 "Pyrococcus horikoshii OT3 genomic DNA, 287001–544000 nt. Position" Jul. 25, 1998.

*Primary Examiner*—Robert A. Wax
*Assistant Examiner*—Bradley S. Mayhew
*Attorney, Agent, or Firm*—Fish & Richardson P.C.

[57] ABSTRACT

A thermostable alpha-glycosidase derived from various *Thermococcus, alcaliphilus AEDII12RA* is disclosed. The enzymes are produced from native or recombinant host cells and can be utilized in the food processing industry.

15 Claims, 3 Drawing Sheets

FIG. 1

```
TTG AGA GCG CTC GTC TTT CAC GGC AAC CTC CAG TAT GCC GAA ATC CCA       48
Leu Arg Ala Leu Val Phe His Gly Asn Leu Gln Tyr Ala Glu Ile Pro
                  5                  10                  15

AAG AGC GAA ATC CCA AAG GTC ATA GAG AAG GCA TAC ATC CCA GTC ATC       96
Lys Ser Glu Ile Pro Lys Val Ile Glu Lys Ala Tyr Ile Pro Val Ile
             20                  25                  30

GAG ACA CTG ATT AAA GAA GAA ATT CCT TTT GGG CTC AAC ATA ACG GGC      144
Glu Thr Leu Ile Lys Glu Glu Ile Pro Phe Gly Leu Asn Ile Thr Gly
         35                  40                  45

TAT ACC TTA AAG TTC CTC CCG CTG AAG GAT ATT ATA GAC CTC GTT AAA GGG  192
Tyr Thr Leu Lys Phe Leu Pro Leu Lys Asp Ile Ile Asp Leu Val Lys Gly
     50                  55                  60

GGC ATC GCG AGT GAC CTT CCC ATA GAG ATA ATC GGA ACG AGC TAC ACG CAC  240
Gly Ile Ala Ser Asp Leu Pro Ile Glu Ile Ile Gly Thr Ser Tyr Thr His
 65                  70                  75                  80

GCA ATA CTC CCC CTC CCG AAG GAA GTA GAA GCA CAA GTT CAG              288
Ala Ile Leu Pro Leu Pro Lys Glu Val Glu Ala Gln Val Gln
             85                  90                  95

AGA GAT AGG GAA GAA AAG GTT AAG GAG CTC TTC GAG CTT TCT CCA AAG GGA  336
Arg Asp Arg Glu Glu Lys Val Lys Glu Leu Phe Glu Leu Ser Pro Lys Gly
             100                 105                 110

TTC TGG CTG CCA GAG CTC CCA TAT GCC CTC GAC CCG ATA ATC CCT ATA CTG  384
Phe Trp Leu Pro Glu Leu Pro Tyr Ala Leu Asp Pro Ile Ile Pro Ile Leu
         115                 120                 125
```

FIG. 1A

```
AAG GAC AAC GGT TAT GAG TAT CTA TTC GCC GAC GGG GAG GCG ATG CTT    432
Lys Asp Asn Gly Tyr Glu Tyr Leu Phe Ala Asp Gly Glu Ala Met Leu
130         135             140

TTC TCA GCT CAT CTC AAC TCG GCG ATA AAA CCA ATT AAA CCG CTC TAT    480
Phe Ser Ala His Leu Asn Ser Ala Ile Lys Pro Ile Lys Pro Leu Tyr
145         150             155             160

CCA CAC CTT ATA AAG GCC CAA AGG CGC TTT AGG TAC ATC AGC
Pro His 3Leu Ile Lys Ala Gln Arg Arg Phe Arg Tyr Ile Ser           528
        165             170             175

TAT CTC GGT CTT AGG GAG CTT AGG TTT AGG ATA AAG CTC GTT TTT
Tyr Leu Gly Leu Arg Glu Leu Arg Phe Arg Ile Lys Leu Val Phe       576
        180             185             190

GAA GGT AAG GTA ACG CTA ACG AAG GCA GTC AAA GAC ATC GAA GCC GTA CCC
Glu Gly Lys Val Thr Leu Thr Lys Ala Val Lys Asp Ile Glu Ala Val Pro 624
        195             200             205

GTT TGG GTG GCC GTG AAC ACG CTA ATG GCT GTA ATG CTC GGC AGG CTT
Val Trp Val Ala Val Asn Thr Leu Met Ala Val Met Leu Gly Arg Leu   672
210             215             220

CCT CTT ATG AAT CCT AAG GTG GCG AGC TGG ATA GAG GAC AAG GAC
Pro Leu Met Asn Pro Lys Val Ala Ser Trp Ile Glu Asp Lys Asp       720
225             230             235             240

AAC ATT CTT CTA TAC GGC ACC GAT ATA GAG TTC ATT GGC TAT AGG GAC
Asn Ile Leu Leu Tyr Gly Thr Asp Ile Glu Phe Ile Gly Tyr Arg Asp   768
        245             250             255
```

FIG. 1B

```
ATT GCA GGC TAC AGA ATG AGT GTT GAG TTA TTA GAG GTT ATA GAC    816
Ile Ala Gly Tyr Arg Met Ser Val Glu Leu Leu Glu Val Ile Asp
        260                 265                 270

GAG CTC AAC TCG GAA CTG TGC CTT CCC TCA GAG CTG AAG CAC ATG GGA    864
Glu Leu Asn Ser Glu Leu Cys Leu Pro Ser Glu Leu Lys His Met Gly
            275                 280                 285

AGG CTC TAC TTA CGG TGC ACT TCG AGT TGG GCA CCA GAT AAG AGC TTG    912
Arg Leu Tyr Leu Arg Cys Thr Ser Ser Trp Ala Pro Asp Lys Ser Leu
        290                 295                 300

AGG ATA TGG AGA GAC GAG AAC GGG GCA AGA CTT AAT ATG CTG TCC    960
Arg Ile Trp Arg Asp Glu Asn Gly Ala Arg Leu Asn Met Leu Ser
        305                 310                 315                 320

TAC AAT ATG AGG GGC GGA GAA GGG GCC CTC CTT GCC GAG AAC AGC GAT GCA    1008
Tyr Asn Met Arg Gly Gly Glu Gly Ala Leu Leu Ala Glu Asn Ser Asp Ala
        325                 330                 335

AGG GGA TGG GAG AGG GGT CCT CTC CCT GAG AGG CTG GAT GCC TTC CGG GCG    1047
Arg Gly Trp Glu Arg Gly Pro Leu Pro Glu Arg Leu Asp Ala Phe Arg Ala
        340                 345                 350

ATA TAT AAC GAT TGG AGG GGT GAA AAT GGG GAA CCT TAG    1086
Ile Tyr Asn Asp Trp Arg Gly Glu Asn Gly Glu Pro End
        355                 360                 365
```

α-GALACTOSIDASE

This invention relates to newly identified polynucleotides, polypeptides encoded by such polynucleotides, the use of such polynucleotides and polypeptides, as well as the production and isolation of such polynucleotides and polypeptides. More particularly, polypeptides of the present invention have been identified as glycosidases and/or α-galactosidases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes for hydrolyzing raffinose (a trisaccharide), converting it to sucrose and galactose. There is application for this enzyme in the beet sugar industry. 20–30% of the domestic U.S. sucrose consumption is sucrose from sugar beets. Raw beet sugar can contain a small amount of raffinose when the sugar beets are stored before processing and rotting begins to set in. Raffinose inhibits the crystallization of sucrose and also constitutes a hidden quantity of sucrose. Thus, there is merit to eliminating raffinose from raw beet sugar. α-galactosidase has also been used as a digestive aid to break down raffinose, stachyose, and verbascose in such foods as beans and other gassy foods.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is an illustration of the full-length DNA and corresponding deduced amino acid sequence of *Thernococcus alcaliphilus* AEDII12RA α-galactosidase 18GC of the present invention. Sequencing was performed using a 378 automated DNA sequencer (Applied Biosystems, Inc.).

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

In accordance with an aspect of the present invention, there are provided isolated nucleic acids (polynucleotides) which encode for the mature enzyme having the deduced amino acid sequence of FIG. 1 (SEQ ID NO:4).

The polynucleotide of this invention was originally recovered from a genomic gene library derived from *Thermococcus alcaliphilus* AEDII12RA, of the genus *Thennococcus*. AEDII12RA grows optimally at 85° C. at pH 9.5.

Accordingly, the polynucleotides and enzymes encoded thereby are identified by the organism from which they were isolated, and are sometimes hereinafter referred to as "AEDII12RA-α-gal-18GC" (FIG. 1 and SEQ ID NOS:3 and 4).

The polypeptide of the present invention shows a protein similarity of 52% and protein identity of 21% to *Dictyoglomus thernophilum* amylase.

This invention, in addition to the isolated nucleic acid molecule encoding the enzyme of the present invention, also provides substantially similar sequences. Isolated nucleic acid sequences are substantially similar if: (i) they are capable of hybridizing under conditions hereinafter described, to the polynucleotide of SEQ ID NO:3; (ii) or they encode DNA sequences which are degenerate to the polynucleotides of SEQ ID NO:3. Degenerate DNA sequences encode the amino acid sequence of SEQ ID NO:4, but have variations in the nucleotide coding sequences. As used herein, substantially similar refers to the sequences having similar identity to the sequences of the instant invention. The nucleotide sequences that are substantially the same can be identified by hybridization or by sequence comparison. Enzyme sequences that are substantially the same can be identified by one or more of the following: proteolytic digestion, gel electrophoresis and/or microsequencing.

One means for isolating the nucleic acid molecules encoding the enzyme of the present invention is to probe a gene library with a natural or artificially designed probe using art recognized procedures (see, for example: Current Protocols in Molecular Biology, Ausubel F. M. et al. (Eds.) Green Publishing Company Assoc. and John Wiley Interscience, New York, 1989, 1992). It will be appreciated by one skilled in the art that the polynucleotides of SEQ ID NOS: 1–2, or fragments thereof (comprising at least 12 contiguous nucleotides), are particularly useful probes. Other particularly useful probes for this purpose are hybridizable fragments of the sequence of SEQ ID NO:3 (i.e., comprising at least 12 contiguous nucleotides).

With respect to nucleic acid sequences which hybridize to specific nucleic acid sequence disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9M NaCl, 50 mM NaH$_2$PO$_4$, pH 7.0, 5.0 mM Na$_2$EDTA, 0.5% SDS, 10X Denhardt's, and 0.5 mg/mL polyriboadenylic acid. Approximately 2×10$^7$ cpm (specific activity 4–9×10$^8$ cpm/μg) of $^{32}$p end-labeled oligonucleotide probe are then added to the solution. After 12–16 hours of incubation, the membrane is washed for 30 minutes at room temperature in 1X SET (150 mM NaCl, 20 mM Tris hydrochloride, pH 7.8, 1 mM Na$_2$EDTA) containing 0.5% SDS, followed by a 30 minute wash in fresh 1X SET at Tm −10° C. for the oligo-nucleotide probe. The membrane is then exposed to auto-radiographic film for detection of hybridization signals.

Stringent conditions means hybridization will occur only if there is at least 90% identity, preferably 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO:3). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence. As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLAST.

The present invention relates to polynucleotides which differ from the reference polynucleotide such that the changes are silent changes, for example the change do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotide of this invention was recovered from a genomic gene library from *Thennococcus alcaliphihes* AEDII12RA. A gene library was generated and excisions were performed according to the protocols/methods hereinafter described.

The polynucleotide of the present invention may be in the form of RNA or DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequence shown in FIG. 1 (SEQ ID NO:3) or may be a different coding sequence, which coding sequence, as a result of the redundancy or degeneracy of the genetic code, encodes the same mature enzyme as the DNA of FIG. 1 (SEQ ID NO:3).

The polynucleotides which encode for the mature enzyme of FIG. 1 (SEQ ID NO:4) may include, but are not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence(s).

The present invention further relates to variants of the herein described polynucleotide which code for fragments, analogs and derivatives of the enzyme having the deduced amino acid sequence of FIG. 1 (SEQ ID NO:4). The variant of the polynucleotide may be a naturally occurring or a non-naturally occurring variant of the polynucleotide.

Thus, the present invention includes polynucleotides encoding the same mature enzyme as shown in FIG. 1 (SEQ ID NO:4) as well as variants of such polynucleotides which variants code for a fragment, derivative or analog of the enzyme of FIG. 1 (SEQ ID NO:4). Such nucleotide variants include deletion variants, substitution variants and addition or insertion variants.

As indicated herein, the polynucleotide may have a coding sequence which is a naturally occurring allelic variant of the coding sequence shown in FIG. 1 (SEQ ID NO:3). As known in the art, an allelic variant is an alternate form of a polynucleotide sequence which may have a substitution, deletion or addition of one or more nucleotides, which does not substantially alter the function of the encoded protein.

Fragments of the fall length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary to that of the gene of the present invention are used to screen a library of genomic DNA to identify members of the library to which the probe hybridizes.

It is also appreciated that such probes can be and are preferably labeled with an analytically detectable reagent to facilitate identification of the probe. Useful reagents include but are not limited to radioactive isotopes, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequence if there is at least 70%, preferably at least 90%, and more preferably at least 95% identity between the sequences. The present invention particularly relates to polynucleotides which hybridize under stringent conditions to the above-described polynucleotide. As herein used, the term "stringent conditions" means hybridization will occur only if there is at least 95% and preferably at least 97% identity between the sequences. The polynucleotides which hybridize to the hereinabove described polynucleotide in a preferred embodiment encode enzymes which either retain substantially the same biological function or activity as the mature enzyme encoded by the DNA of FIG. 1 (SEQ ID NO:3).

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotide of SEQ ID NO:3, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzyme of SEQ ID NO:4 as well as fragments thereof, which fragments have at least 15 bases, preferably at least 30 bases and most preferably at least 50 bases, which fragments are at least 90% identical, preferably at least 95% identical and most preferably at least 97% identical under stringent conditions to any portion of a polynucleotide of the present invention.

The present invention further relates to an enzyme which has the deduced amino acid sequence of FIG. 1 (SEQ ID NO:4) as well as fragments, analogs and derivatives thereof.

The terms "fragment," "derivative" and "analog" when referring to the enzyme of FIG. 1 (SEQ ID NO:4) mean enzymes which retain essentially the same biological function or activity as the enzyme of SEQ ID NO:4. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 (SEQ ID NO:4) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzyme and polynucleotide of the present invention are preferably provided in an isolated form, and preferably are purified to homogeneity. The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzyme of SEQ ID NO:4 (in particular the mature enzyme) as well as enzymes which have at least 70% similarity (preferably at least 70% identity) to the enzyme of SEQ ID NO:4 and more preferably at least 90% similarity (more preferably at least 90% identity) to the enzyme of SEQ ID NO:4 and still more preferably at least 95% similarity (still more preferably at least 95% identity) to the enzyme of SEQ ID NO:4 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination. Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS (Stratagene), ptrc99a, pKK223-3, pDR540, pRIT2T (Pharmacia); Eukaryotic: pXT1, pSG5 (Stratagene) pSVK3, pBPV, pMSG, pSVL, SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzyme of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzimnan, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzyme of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The polynucleotide of this invention was recovered from a genomic gene library from *Thernococcus alcaliphilus* AEDII12RA. The gene library was generated in the λZAP2 cloning vector (Stratagene). Mass excisions were performed on these libraries to generate libraries in the pBluescript phagemid. Libraries were generated and excisions were performed according to the protocols/methods hereinafter described.

EXAMPLE 1

Production of the Expression Gene Bank

Colonies containing pBluescript plasmids with random inserts from the organism *Thermococcus alcaliphilus* AEDII12RA were obtained from an original XZAP2 genomic library generated according to the manufacturer's (Stratagene) protocol. The clones were then excised from λZAP2 to pBluescript. The clones were excised to pBluescript according to the method of Hay and Short. (Hay, B. and Short, J. *Strategies*, 1992, 5:16.) The resulting colonies were picked with sterile toothpicks and used to singly inoculate each of the wells of 96-well microtiter plates. The wells contained 250 μL of LB media with 100 μg/ml methicillin, and 10% v/v glycerol (LB Amp/Meth, glycerol). The cells were grown overnight at 37° C. without shaking. This constituted generation of the "Source GeneBank"; each well of the Source GeneBank thus contained a stock culture of *E. coli* cells, each of which contained a pBluescript plasmid with a unique DNA insert.

EXAMPLE 2

Screening for Glycosidase Activity

The plates of the Source GeneBank were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 10 to 12 different pBluescript clones from each of the source library plates. The Condensed Plate was grown for 16 h at 37° C. and then used to inoculate two white 96-well Polyfiltronics microtiter daughter plates containing in each well 250 μL of LB Amp/Meth (without glycerol). The original condensed plate was put in storage −80° C. The two condensed daughter plates were incubated at 37° C. for 18 h.

A '600 μM substrate stock solution' was prepared as follows: 25 mg of each of four compounds was dissolved in the appropriate volume of DMSO to yield a 25.2 mM solution. The compounds used were 4-methylumbelliferyl β-D-xyloside, 4-methylumbelliferyl α-D-galactoside, 4-methylumbelliferyl α-D-mannopyranoside, and 4-methylumbelliferyl β-D-mannopyranoside. Two hundred fifty microliters of each DMSO solution was added to ca. 9 mL of 50 mM, pH 7.5 Hepes buffer. The volume was taken to 10.5 mL with the above Hepes buffer to yield a clear solution. All four umbelliferones were obtained from Sigma Chemical Co.

Fifty μL of the '600 μM stock solution' was added to each of the wells of a white condensed plate using the Biomek to yield a final concentration of substrate of ~100 μM. The fluorescence values were recorded (excitation=326 nm, emission=450 nm) on a plate reading fluorometer immediately after addition of the substrate. The plate was incubated at 70° C. for 60 min and the fluorescence values were recorded again. The initial and final fluorescence values were subtracted to determine if an active clone was present by an increase in fluorescence over the majority of the other wells.

EXAMPLE 3

Isolation of Active Clone and Substrate Specificity Determination

In order to isolate the individual clone which carried the activity, the Source GeneBank plates were thawed and the individual wells used to singly inoculate a new plate containing LB/Amp/Meth. As above the plate was incubated at 37° C. to grow the cells, the 50 μL of 600 μM substrate stock solution added using the Biomek. Once the active well from the source plate was identified, the cells from the source plate were streaked on agar with LB/Amp/Meth and grown overnight at to 37° C. to obtain single colonies. Eight single colonies were picked with a sterile toothpick and used to singly inoculate the wells of a 96-well microtiter plate. The wells contained 250 μL of LB/Amp/Meth. The cells were grown overnight at 37° C. without shaking. A 200 ||L aliquot was removed from each well and assayed with the substrates as above. The most active clone was identified and the remaining 50 μL of culture was used to streak an agar plate with LB/Amp/Meth. Eight single colonies were picked, grown and assayed as above. The most active clone was used to inoculate 3 mL cultures of LB/Amp/Meth, which were grown overnight. The plasmid DNA was isolated from the cultures and utilized for sequencing. Colonies from this final streak onto the agar plate were also used to inoculate wells containing 250 μL of LB/Amp/Meth. In addition, colonies containing plasmids with no inserts were used as negative controls. A 600 μM solution of each individual substrate was made up for the purpose of determining the substrate specificity of the enzyme. Fifty μL of each of the four substrates were added individually to the test and control wells and assayed for activity as above. Only the wells which contained the 4-methylumbelliferyl α-D-galactoside showed an increase in fluorescence indicating activity.

Numerous modifications and variations of the present invention are possible in light of the above teachings and, therefore, within the scope of the appended claims, the invention may be practiced otherwise than as particularly described.

What is claimed is:

1. A substantially purified enzyme selected from the group consisting of:

(a) an enzyme comprising the amino acid sequence as set forth in SEQ ID NO:4; and (b) an enzyme comprising 30 contiguous amino acids from SEQ ID NO:4 wherein said enzyme has α-galactosidase activity.

2. A method for hydrolyzing α-galactose bonds comprising:

contacting a compound having α-galactose bonds with an effective amount of a substantially purified enzyme having the amino acid sequence set forth in SEQ ID NO:4.

3. An isolated polynucleotide encoding the amino acid sequence as set forth in SEQ ID NO:4.

4. An isolated polynucleotide encoding an enzyme having α-galactosidase activity selected from the group consisting of:

a) SEQ ID NO:3;

b) SEQ ID NO:3, wherein T can also be U;

c) nucleic acid sequences complementary to SEQ ID NO:3; and a polynucleotide encoding an enzyme comprising 30 contiguous amino acids from SEQ ID NO:4 wherein said enzyme has α-galactosidase activity.

5. An expression vector containing a polynucleotide of claim 3.

6. The expression vector of claim 5, wherein the vector is a plasmid.

7. The expression vector of claim 5, wherein the vector is a viral vector.

8. The polynucleotide of claim 3, wherein the polynucleotide sequence is from *Thermococcus*.

9. A host cell transformed with the expression vector of claim 5.

10. The host cell of claim 9, wherein the cell is a eukaryotic cell.

11. The host cell of claim 9, wherein the cell is a prokaryotic cell.

12. A method of producing an α-galactosidase polypeptide comprising:

a) transforming a host cell with a polynucleotide of claim 3;

b) expressing the polynucleotide; and c) recovering the α-galactosidase polypeptide.

13. The method of claim 12, wherein the host cell is a prokaryotic cell.

14. The method of claim 12, wherein the host cell is a eukaryotic cell.

15. A substantially purified polypeptide having the amino acid sequences as set forth in SEQ ID NO:4.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CCGAGAATTC ATTAAAGAGG AGAAATTAAC TATGAGAGCG CTCGTCTTTC AC      52

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CGGAAGATCT AGGTTCCCCA TTTTCACCCC T      31

(2) INFORMATION FOR SEQ ID NO:3:

(i) SEQUENCE CHARACTERISTICS:
      (A) LENGTH: 1041 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 1...1038
      (D) OTHER INFORMATION:

(xi) SEQUENCE DESCRIPTION: SEQ ID NO:3:

TTG AGA GCG CTC GTC TTT CAC GGC AAC CTC CAG TAT GCC GAA ATC CCA      48
Leu Arg Ala Leu Val Phe His Gly Asn Leu Gln Tyr Ala Glu Ile Pro
1            5                    10              15

AAG AGC GAA CCA AAG GTC ATA GAG AAG GCA TAC ATC CCA GTC ATC GAG      96
Lys Ser Glu Pro Lys Val Ile Glu Lys Ala Tyr Ile Pro Val Ile Glu

-continued

```
                    20                  25                  30
ACA CTG ATT AAA GAA GAA CCT TTT GGG CTC AAC ATA ACG GGC TAT ACC        144
Thr Leu Ile Lys Glu Glu Pro Phe Gly Leu Asn Ile Thr Gly Tyr Thr
            35                  40                  45

TTA AAG TTC CTC CCG AAG GAT ATT ATA CTC GTT AAA GGG GGC ATC GCG        192
Leu Lys Phe Leu Pro Lys Asp Ile Ile Leu Val Lys Gly Gly Ile Ala
    50                  55                  60

AGT GAC CTG ATA GAG ATA ATC GGA ACG AGC TAC ACG GCA ATA CTC CCC        240
Ser Asp Leu Ile Glu Ile Ile Gly Thr Ser Tyr Thr Ala Ile Leu Pro
65                  70                  75                  80

CTC CTG CCG CTT AGC AGA GTA GAA GCA CAA GTT CAG AGA GAT AGG GTT        288
Leu Leu Pro Leu Ser Arg Val Glu Ala Gln Val Gln Arg Asp Arg Val
                85                  90                  95

AAG GAA GAG CTC TTC GAG GTT TCT CCA AAG GGA TTC TGG CTG CCA GAG        336
Lys Glu Glu Leu Phe Glu Val Ser Pro Lys Gly Phe Trp Leu Pro Glu
            100                 105                 110

CTC GCC GAC CCG ATA ATC CCT GCC ATA CTG AAG GAC AAC GGT TAT GAG        384
Leu Ala Asp Pro Ile Ile Pro Ala Ile Leu Lys Asp Asn Gly Tyr Glu
    115                 120                 125

TAT CTA TTC GCC GAC GAG GCG ATG CTT TTC TCA GCT CAT CTC AAC TCG        432
Tyr Leu Phe Ala Asp Glu Ala Met Leu Phe Ser Ala His Leu Asn Ser
130                 135                 140

GCG ATA AAG CCA ATT AAA CCG CTC CCA CAC CTT ATA AAG GCC CAA AGG        480
Ala Ile Lys Pro Ile Lys Pro Leu Pro His Leu Ile Lys Ala Gln Arg
145                 150                 155                 160

GAA AAG CGC TTT AGG TAC ATC AGC TAT CTC CTT CTC AGG GAG CTT AGG        528
Glu Lys Arg Phe Arg Tyr Ile Ser Tyr Leu Leu Leu Arg Glu Leu Arg
                165                 170                 175

AAG GCG ATA AAG CTC GTT TTT GAA GGT AAG GTA ACG CTA AAG GTC AAA        576
Lys Ala Ile Lys Leu Val Phe Glu Gly Lys Val Thr Leu Lys Val Lys
            180                 185                 190

GAC ATC GAA GCC GTA CCC GTT TGG GTG GCC GTG AAC ACG GCT GTA ATG        624
Asp Ile Glu Ala Val Pro Val Trp Val Ala Val Asn Thr Ala Val Met
    195                 200                 205

CTC ATC GGA AGG CTT CCT CTT ATG AAT CCT AAG AAA GTG GCG AGC TGG        672
Leu Ile Gly Arg Leu Pro Leu Met Asn Pro Lys Lys Val Ala Ser Trp
210                 215                 220

ATA GAG GAC AAG AAC ATT CTT CTA TAC GGC ACC GAT ATA GAG TTC ATT        720
Ile Glu Asp Lys Asn Ile Leu Leu Tyr Gly Thr Asp Ile Glu Phe Ile
225                 230                 235                 240

GGC TAT AGG GAC ATT GCA GGC AGA ATG AGT GTT GAG GGA TTA TTA GAG        768
Gly Tyr Arg Asp Ile Ala Gly Arg Met Ser Val Glu Gly Leu Leu Glu
                245                 250                 255

GTT ATA GAC GAG CTC AAC TCG GAA CTG TGC CCC TCA GAG CTG AAG CAC        816
Val Ile Asp Glu Leu Asn Ser Glu Leu Cys Pro Ser Glu Leu Lys His
            260                 265                 270

AGT GGA AGG GAG CTC TAC TTA CGG ACT TCG AGT TGG GCA GAT AAG AGC        864
Ser Gly Arg Glu Leu Tyr Leu Arg Thr Ser Ser Trp Ala Asp Lys Ser
    275                 280                 285

TTG AGG ATA TGG AGA GAG GAC GAA GGG AAC GCA AGA CTT AAT ATG CTG        912
Leu Arg Ile Trp Arg Glu Asp Glu Gly Asn Ala Arg Leu Asn Met Leu
290                 295                 300

TAC AAT ATG AGG GGC GAA CTC GCC TTT TTA GCC GAG AAC AGC GAT GCA        960
Tyr Asn Met Arg Gly Glu Leu Ala Phe Leu Ala Glu Asn Ser Asp Ala
305                 310                 315                 320

AGG GGA TGG CCC CTC CCT GAG AGG AGG CTG GAT GCC TTC CGG GCG ATA       1008
Arg Gly Trp Pro Leu Pro Glu Arg Arg Leu Asp Ala Phe Arg Ala Ile
                325                 330                 335

TAT AAC GAT TGG AGG GGT AAT GGG GAA CCT TAG                           1041
Tyr Asn Asp Trp Arg Gly Asn Gly Glu Pro
```

340            345

(2) INFORMATION FOR SEQ ID NO:4:

(i) SEQUENCE CHARACTERISTICS:
        (A) LENGTH: 346 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

```
Leu Arg Ala Leu Val Phe His Gly Asn Leu Gln Tyr Ala Glu Ile Pro
 1               5                  10                  15

Lys Ser Glu Pro Lys Val Ile Glu Lys Ala Tyr Ile Pro Val Ile Glu
                20                  25                  30

Thr Leu Ile Lys Glu Glu Pro Phe Gly Leu Asn Ile Thr Gly Tyr Thr
                35                  40                  45

Leu Lys Phe Leu Pro Lys Asp Ile Ile Leu Val Lys Gly Gly Ile Ala
            50                  55                  60

Ser Asp Leu Ile Glu Ile Ile Gly Thr Ser Tyr Thr Ala Ile Leu Pro
 65                  70                  75                  80

Leu Leu Pro Leu Ser Arg Val Glu Ala Gln Val Gln Arg Asp Arg Val
                85                  90                  95

Lys Glu Glu Leu Phe Glu Val Ser Pro Lys Gly Phe Trp Leu Pro Glu
                100                 105                 110

Leu Ala Asp Pro Ile Ile Pro Ala Ile Leu Lys Asp Asn Gly Tyr Glu
                115                 120                 125

Tyr Leu Phe Ala Asp Glu Ala Met Leu Phe Ser Ala His Leu Asn Ser
            130                 135                 140

Ala Ile Lys Pro Ile Lys Pro Leu Pro His Leu Ile Lys Ala Gln Arg
145                 150                 155                 160

Glu Lys Arg Phe Arg Tyr Ile Ser Tyr Leu Leu Leu Arg Glu Leu Arg
                165                 170                 175

Lys Ala Ile Lys Leu Val Phe Glu Gly Lys Val Thr Leu Lys Val Lys
                180                 185                 190

Asp Ile Glu Ala Val Pro Val Trp Val Ala Val Asn Thr Ala Val Met
                195                 200                 205

Leu Ile Gly Arg Leu Pro Leu Met Asn Pro Lys Lys Val Ala Ser Trp
            210                 215                 220

Ile Glu Asp Lys Asn Ile Leu Leu Tyr Gly Thr Asp Ile Glu Phe Ile
225                 230                 235                 240

Gly Tyr Arg Asp Ile Ala Gly Arg Met Ser Val Glu Gly Leu Leu Glu
                245                 250                 255

Val Ile Asp Glu Leu Asn Ser Glu Leu Cys Pro Ser Glu Leu Lys His
                260                 265                 270

Ser Gly Arg Glu Leu Tyr Leu Arg Thr Ser Ser Trp Ala Asp Lys Ser
            275                 280                 285

Leu Arg Ile Trp Arg Glu Asp Glu Gly Asn Ala Arg Leu Asn Met Leu
290                 295                 300

Tyr Asn Met Arg Gly Glu Leu Ala Phe Leu Ala Glu Asn Ser Asp Ala
305                 310                 315                 320

Arg Gly Trp Pro Leu Pro Glu Arg Arg Leu Asp Ala Phe Arg Ala Ile
                325                 330                 335

Tyr Asn Asp Trp Arg Gly Asn Gly Glu Pro
```